United States Patent [19]

Iovine et al.

[11] 4,104,307

[45] Aug. 1, 1978

[54] PROCESS FOR PREPARING 2-AMINOALKYL HALIDE BISULFATE SALTS

[75] Inventors: Carmine P. Iovine, Somerset; Dilip K. Ray-Chaudhuri, Bridgewater, both of N.J.

[73] Assignee: National Starch and Chemical Corporation, Bridgewater, N.J.

[21] Appl. No.: 757,633

[22] Filed: Jan. 7, 1977

[51] Int. Cl.$^2$ ............................................. C07C 85/24
[52] U.S. Cl. ........................... 260/583 G; 260/652 R; 260/563 R; 260/563 C; 260/694
[58] Field of Search ........... 260/583 G, 563 R, 563 C, 260/694, 652 R

[56] References Cited

U.S. PATENT DOCUMENTS

| 1,470,656 | 10/1923 | Traube | 260/652 R |
| 2,016,072 | 10/1935 | Calcott et al. | 260/652 R X |
| 2,660,602 | 11/1953 | Wiese | 260/652 R X |
| 3,080,431 | 3/1963 | Zappel et al. | 260/652 R X |
| 3,153,096 | 10/1964 | Soenksen et al. | 260/583 G |

OTHER PUBLICATIONS

Groggins, "Unit Processes in Organic Synthesis", 5th ed., p. 724 (1958).
Karrer, "Organic Chemistry", 4th ed., p. 112 (1950).
Datta et al., "JACS", vol. 43, pp. 303–315 (1921).

Primary Examiner—Winston A. Douglas
Assistant Examiner—John J. Doll
Attorney, Agent, or Firm—James & Franklin

[57] ABSTRACT

An improved process for preparing 2-aminoalkyl halide bisulfate salts comprises reacting dry hydrogen halide with 2-aminoalkyl monosulfate esters. The 2-aminoalkyl halide bisulfate salts resulting therefrom are produced in high yields and are used industrially to prepare cationic starch and cellulose derivatives.

14 Claims, No Drawings

PROCESS FOR PREPARING 2-AMINOALKYL HALIDE BISULFATE SALTS

BACKGROUND OF THE INVENTION

This invention relates to a novel process for preparing 2-aminoalkyl halide bisulfate salts. More particularly, this invention is directed to an improved process for preparing 2-aminoalkyl halide bisulfate salts in high yields which is economical and in which essentially no by-products are formed.

The use of 2-aminoalkyl halide bisulfate salts in industry to prepare cationic aminoalkyl starch and cellulose derivatives is well known. Derivatives of this type find use in many applications including, for example, in the treatment of waste water, as retention and strength aids in the papermaking process, as coating vehicles, and as ion-exchange resins.

Prior art techniques for preparing 2-aminoalkyl halide bisulfate salts are documented in the literature. Among these are included processes which involve reacting 2-aminoalcohols with such halogenating agents as thionyl chloride, phosphorus halides, hydrogen halides and phosgene (as described in U.S. Pat. Nos. 2,136,171 and 3,153,096; French Patent No. 1,383,121; and British Patent No. 402,159). Such processes are not attractive industrially since they either involve the disposal of large amounts of reaction by-product, as when thionyl chloride and phosphorus halides are employed, or they require special equipment and high pressure techniques, as when hydrogen halide is employed.

It is accordingly an object of the present invention to provide an improved process for preparing 2-aminoalkyl halide bisulfate salts in high yields which is very economical.

It is another object to provide a process for preparing 2-aminoalkyl halide bisulfate salts which involves no special equipment.

It is a further object to provide a process for preparing 2-aminoalkyl halide bisulfate salts in which essentially no by-products are formed.

SUMMARY OF THE INVENTION

The above and related objects are achieved in a process for preparing 2-aminoalkyl halide bisulfate salts of the general formula:

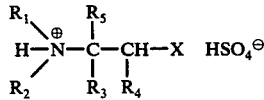

wherein $R_1$ is selected from the group consisting of alkyl ($C_1$ to $C_{18}$), cycloalkyl and hydrogen; $R_2$ is selected from the group consisting of alkyl ($C_1$ to $C_{18}$) and cycloalkyl; $R_3$, $R_4$ and $R_5$ are selected independently from the group consisting of alkyl ($C_1$ to $C_3$) and hydrogen; and X is selected from the group consisting of Cl and Br.

The process comprises reacting dry hydrogen halide, selected from the group consisting of hydrogen chloride and hydrogen bromide, with the corresponding 2-aminoalkyl monosulfate ester of the general formula:

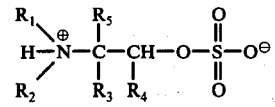

wherein $R_1$, $R_2$, $R_3$, $R_4$ and $R_5$ are all as defined above, the temperature of the reaction being maintained at 100° – 200° C.

DETAILED DESCRIPTION OF THE PREFERRED EMBODIMENTS

The process of this invention embodies two variations depending on whether the intermediate 2-aminoalkyl monosulfate ester and the hydrogen halide are prepared in situ or whether the monosulfate ester is prepared in a separate step, with the hydrogen halide being added directly thereto.

The variation wherein the 2-aminoalkyl monosulfate ester and hydrogen halide are prepared in situ involves reacting the corresponding halosulfonic acid with a 2-amino-alcohol, or its hydrohalide salt, of the general formula:

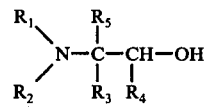

wherein $R_1$, $R_2$, $R_3$, $R_4$ and $R_5$ are all as defined above and the hydrohalide salt thereof is a hydrochloride or hydrobromide salt. In this variation the resultant 2-aminoalkyl halide bisulfate salt is prepared directly in one step. Suitable 2-aminoalcohols include, for example, N,N-diethyl-2-aminoethanol, N-methyl-2-aminoethanol, N,N-dimethyl-2-amino-2-methyl-1-propanol, N-methyl-2-amino-1-butanol, N-stearyl-N-methyl-2-aminoethanol, N-methyl-2-amino-1-ethyl-1-pentanol, N-cyclohexyl-N-methyl-2-aminoethanol, and the like. Suitable hydrohalide salts are exemplified by N,N-diethyl-2-aminoethanol hydrochloride, N-methyl-2-aminoethanol hydrobromide, etc.

The other variation of this process wherein the 2-aminoalkyl monosulfate ester is prepared in a separate step involves reacting the 2-aminoalcohol as defined above with a sulfating agent to produce the monosulfate ester, which is then reacted with dry hydrogen halide in a second step to obtain the final product.

The two variations are further described hereinafter.

One-Step Variation: Monosulfate ester prepared in situ

Halosulfonic acid is added to the 2-aminoalcohol or the hydrohalide salt thereof, with the reaction being carried out either neat (i.e., without solvent) or in a suitable solvent which is inert to sulfation. Typical solvents which may be used include aliphatic hydrocarbons such as, for example, decalin, octane, decane, or in general any high-boiling paraffin. Aromatic solvents and those with reactive functional groups should be avoided. The reaction is preferably carried out neat.

Use of the hydrohalide salt of the 2-aminoalcohol as opposed to using the 2-aminoalcohol itself results in higher yields of product and is therefore preferred. The hydrogen halide gas which is generated as a by-product of the reaction when the hydrohalide salt is employed is then reacted with additional 2-aminoalcohol to regenerate the hydrohalide salt, and the cycle is repeated indefinitely. The hydrohalide salt is produced initially by adding gaseous or aqueous hydrogen halide, i.e., hydrogen chloride or hydrogen bromide, in about stoichiometric amounts to the 2-aminoalcohol over a period of about 1 – 2 hours with agitation and cooling so that the temperature of the reaction rises gradually to about 100° – 200° C., preferably 120° – 150° C., at the end of the reaction. If aqueous hydrogen halide is employed, the water is removed from the product prior to further reaction. Halosulfonic acid is then added to the molten salt. The preferred hydrohalide salt is the hydrochloride salt.

The amount of halosulfonic acid employed may range from about stoichiometric to 15 mole percent excess.

The halosulfonic acid is added over a period of about 2 – 6 hours, depending on such factors as the particular alcohol used, the reaction temperature and the scale of the reaction. After addition the reaction mixture is allowed to stand for an additional period of about 1 – 3 hours to insure complete reaction, the reaction thus being carried out for a total of about 3 – 9 hours.

The temperature of the reaction throughout the addition and during the period thereafter is maintained at about 100° – 200° C., depending on the particular alcohol employed. The temperature is preferably maintained at 120° – 150° C. Reactions run at temperatures below about 100° C. do not result in the high yields (above 85%) characteristic of this invention.

At the end of the reaction, the reaction mixture is cooled and the resultant 2-aminoalkyl halide bisulfate salt isolated by addition of water and/or steam over a period of 15 minutes to the cooled reaction mixture.

Two-Step Variation: Monosulfate ester prepared in a separate step

Procedures for preparing the 2-aminoalkyl monosulfate ester intermediates employed in this invention are well known and described in the art (see U.S. Pat. Nos. 3,169,143 and 3,194,826, and British Patent No. 938,053). In the preparation of these intermediates, the 2-aminoalcohol is reacted either neat or in a solvent inert to sulfation with a sulfating agent such as sulfur trioxide, sulfuric acid or oleum (i.e., a mixture of sulfuric acid and sulfur trioxide). In the latter two cases, the reaction is driven to completion by the removal of water produced in the esterification. The resultant monosulfate esters are inner salts (zwitterions) and need not be purified (or in some cases even isolated) prior to further use. If a solvent is used in the sulfation step, it may be removed before conducting the hydrohalogenation step.

To the monosulfate ester thus prepared is subsequently added dry gaseous hydrogen halide, with the reaction being carried out either neat (the preferred procedure) or in a suitable solvent, which, in this variation, includes aliphatic, aromatic and chlorinated hydrocarbons. Typical useful solvents include all of those suitable for the one-step variation as well as dichlorobenzene, tetrachloroethylene, p-xylene, etc.

The amount of hydrogen halide employed is the same as the amount of halosulfonic acid used in the one-step variation described above, i.e., about stoichiometric to 15 mole percent excess.

The addition of hydrogen halide is carried out until the desired amount is consumed, i.e., in a period of about 2 – 4 hours. The reaction mixture is allowed to stand for an additional period of about 1 – 3 hours, the reaction being thus carried out for a total of about 3 – 7 hours.

The temperature of the reaction upon addition of hydrogen halide and during the period thereafter is the same as that described above for the one-step variation, i.e., 100° – 200° C., and preferably 120° – 150° C. After reaction the resultant 2-aminoalkyl halide bisulfate salt is isolated as described above.

EXAMPLES

The following examples will illustrate the practice of this invention but are not intended to limit its scope. In all of the examples all parts and percentages are given by weight and all temperatures in degrees Celsius unless otherwise noted.

EXAMPLE 1

This example illustrates the preparation of a 2-aminoalkyl halide bisulfate salt by the one-step variation of the process of this invention using N,N-diethyl-2-aminoethanol as the starting 2-aminoalcohol.

When the hydrochloride salt of N,N-diethyl-2-aminoethanol is utilized, a cyclic process is initiated, represented by the following reaction sequence, which is not limited to the particular 2-aminoalcohol nor to the particular halide of this example. This sequence clearly demonstrates the economic advantage of the process of this invention over the prior art:

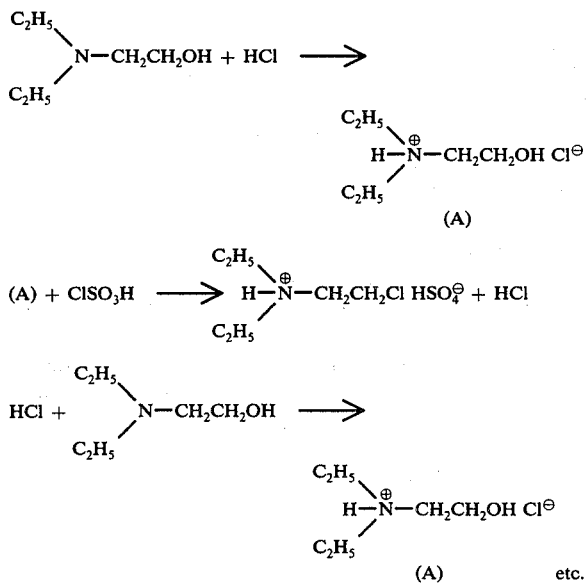

The reactor assembly employed herein consisted of a one-liter four-neck flask fitted with a glass thermometer, coil condenser and equalized dropping funnel. A scrubber train attached to the condenser was connected to a similar reactor assembly by a subsurface gas inlet tube.

In the preparation of the hydrochloride salt, the reactor was charged with 234 g. of N,N-diethyl-2-aminoethanol. A total of 81 g. of hydrogen chloride gas was then added over a period of 1.5 hours with agitation and cooling so that the temperature of the molten mixture was controlled to gradually reach 135° – 140° C. by the end of the addition.

To the resultant molten hydrochloride salt was slowly added a total of 268 g. of chlorosulfonic acid over a period of 3 hours, with the temperature being maintained at 135° – 140° C. throughout the addition. The hydrogen chloride gas evolved in the course of the reaction was scrubbed through the train of the condenser into the second reactor, which contained 234 g. of N,N-diethyl-2-aminoethanol. The temperature in the second reactor was controlled over a 3-hour period to a maximum of 135° C.

After the addition of chlorosulfonic acid was complete, the reaction mixture in the original reactor was stirred for an additional one hour at 135° – 140° C. At the end of this period the scrubber train was disconnected, the reaction mixture cooled to 70° C., and 350 g. of distilled water added over a period of 15 minutes. The resulting aqueous solution was amber in color and contained 434.3 g. (93.1% yield) of N,N-diethyl-2-aminoethyl chloride bisulfate salt.

The N,N-diethyl-2-aminoethanol hydrochloride salt prepared in the second reactor by scrubbing the hydrogen chloride evolved from the initial reaction was then reacted with chlorosulfonic acid in a similar manner to produce a second batch of product and the cyclic process repeated several times. The results obtained are given in Table I.

Using the same procedure (omitting the step of forming the hydrochloride salt), N,N-diethyl-2-aminoethanol may be directly reacted with chlorosulfonic acid. When the N,N-diethyl-2-aminoethanol itself is utilized, a reaction occurs according to the following equation, which is representative of the manner in which all the 2-aminoalcohols of this invention react with halosulfonic acid:

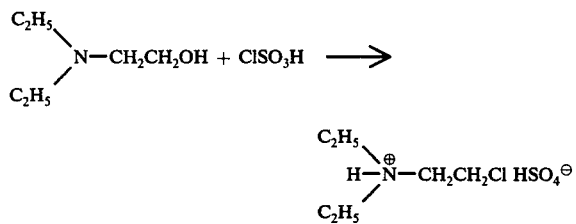

In this case, the 2-aminoalcohol is partially converted to the 2-aminoalkyl chloride bisulfate salt during addition of chlorosulfonic acid thereto. The conversion is completed during the scrubbing operation or when the hydrogen chloride prepared in situ is recycled into the batch from which it was generated.

TABLE I

| Cycle No. | Weight HCl Transferred to Scrubber (g.) | Weight of Final Product (g.) | % Cl Ionic | % Cl Covalent | % Yield of Final Product |
|---|---|---|---|---|---|
| 0 (initial) | 76.9 | 855 | 2.35 | 7.73 | 93.1 |
| 1 | 78.0 | 856 | 2.30 | 7.78 | 93.8 |
| 2 | 79.0 | 855 | 2.13 | 7.58 | 91.3 |
| 3 (Final) | 81.7 | 856 | 1.78 | 7.67 | 92.5 |

A differential chloride procedure was used to obtain the ionic and covalent chloride contents of the product. This procedure essentially comprised utilizing the Volhard analysis for chloride in determining first the percent ionic chloride present (i.e., the amount of chloride not covalently bonded to the 2-chloroalkyl amine portion of the product) and in determining secondly the percent total chloride present (i.e., the sum of the amount of ionic chloride and the amount of covalent chloride) by subjecting the reaction product to hydrolysis using potassium hydroxide. From the ionic and total chloride contents the amount of organic chloride and the percent yield of product could be determined.

EXAMPLE 2

This example illustrates the preparation of the 2-aminoalkyl chloride bisulfate salt of Example 1 by the two-step variation of the process of this invention using sulfuric acid as the sulfating agent. The following schematic equations illustrate the reactions involved but are not limited to the particular 2-aminoalcohol and hydrogen halide of this example:

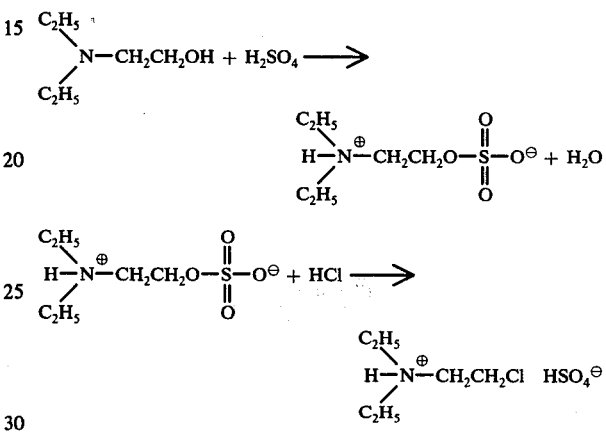

SULFATION STEP

A two-liter four-neck flask fitted with a glass thermometer, a mechanically-driven glass/Teflon (Registered Trademark of E. I. duPont de Nemours & Co., Inc.) stirrer assembly and a distillation condenser with a collecting flask attached thereto was charged with 107.9 g. of concentrated sulfuric acid (95.5% assay). A total of 120.1 g. of N,N-diethyl-2-aminoethanol was then added over a period of 30 minutes, with the temperature rising to 175° – 180° C. by the end of the addition. With this temperature being maintained, the reaction flask was evacuated very slowly subsequent to addition. When the pressure stabilized at 1 – 5 mm Hg, the reaction mixture was heated at 175° – 180° C. for an additional 2.5 hours. Upon analysis, the reaction mixture was found to have a monosulfate ester activity of 91.4%, corresponding to a calculated yield of 95.5% of N,N-diethyl-2-aminoethyl monosulfate ester. The reaction mixture was cooled to 135° – 140° C. without isolating the product therefrom.

HYDROCHLORINATION STEP

The flask assembly containing the cooled reaction mixture was fitted with a means of gas introduction, and a total of 40.3 g. of hydrogen chloride gas was bubbled into the reaction mixture for a period of 2.5 hours at 135° – 140° C. After the addition was complete, the reaction mixture was maintained at 135° – 140° C. for about 2 hours. At the end of this period, the reaction mixture was cooled to 75° C. and 150 g. of distilled water added over a period of 15 minutes. The resultant aqueous solution was amber in color and weighed 395 g. Analysis of the resulting product mixture using the differential chloride technique yielded the following data:

| Moles of Total Covalent Chloride | % Chloride Ionic | % Chloride Covalent | Total | % Yield of N,N-diethyl-2-aminoethyl chloride bisulfate salt |
|---|---|---|---|---|
| 0.91 | 1.75 | 8.10 | 9.85 | 97 (based on monosulfate ester) |

EXAMPLE 3

This example illustrates the preparation of N,N-diethyl-2-aminoethyl chloride bisulfate salt by the two-step variation process using other sulfating agents. The procedure described in Example 2 was basically followed except that different reaction times and temperatures were employed. The reaction conditions and results are given in Table II. It can be seen that sulfating agents other than sulfuric acid are equally effective in obtaining high yields of product.

EXAMPLES 4 – 9

These examples illustrate the preparation of several 2-aminoalkyl halide bisulfate salts by the two variations of the process of this invention using the basic procedures described in Examples 1 and 2. The results are given in Table III.

EXAMPLE 10

This example illustrates the use of a 2-aminoalkyl chloride bisulfate salt produced by the process of this invention in preparing a useful cationic starch derivative.

A 500-ml. flask equipped with a stirrer, condenser, thermometer and an acid trap was charged with 125 parts distilled water, 113.6 parts corn starch (with a moisture content of 12%) and 2.5 parts calcium hydroxide. The mixture was agitated at room temperature for 15 minutes and 8.95 parts 50.8% aqueous solution of the N,N-diethyl-2-aminoethyl chloride bisulfate salt prepared in the initial batch of Example 1 was then added. The resulting reaction mixture was stirred and heated at 40° C. for a period of 6 hours. After this period the reaction mixture was cooled and acidified to pH 3.5 with a 3:1 water:hydrochloric acid solution, filtered, and washed several times by resuspension and filtration. The final product after drying contained 9.2% water and 0.27% nitrogen (dry basis). The yield of N,N-diethyl-2-aminoethyl ether starch was 96.4% based on nitrogen.

TABLE II

| Sulfating Agent | Moles of Sulfating Agent | Moles of DEAE[a] | Temperature (° C.) | Time (hrs.) | Moles of HCl | Temperature (° C.) | Time[b] (hrs.) | Yield (%) |
|---|---|---|---|---|---|---|---|---|
| 2.5% oleum[c] | 2.63 | 2.50 | 155 | 2 | 2.75 | 135 | 3 | 94 |
| 20% oleum | 2.50 | 2.50 | 150 | 2.5 | 2.50 | 140 | 3 | 95 |
| SO$_3$[d] | 2.00 | 2.00 | 20 | 1 | 2.10 | 135 | 3.5 | 93 |

[a]DEAE = N,N-diethyl-2-aminoethanol
[b]This represents the total time, i.e., the amount of time allowed for addition of HCl and for subsequent heating.
[c]The percent oleum is the percentage of sulfur trioxide by weight in the composition.
[d]Sulfation step run in 1,2-dichloroethane; solvent removed prior to hydrochlorination step.

TABLE III

| EXAMPLE | 4 | 5 | 6 | 7 | 8 | 9 |
|---|---|---|---|---|---|---|
| INGREDIENT, parts | | | | | | |
| N,N-dimethyl-2-aminoethanol | 89 | 89 | | | | |
| N-methyl-2-aminoethanol | | | 112.5 | | | |
| N,N-dimethyl-2-aminopropanol | | | | 206.4 | | |
| N,N-diethyl-2-aminoethanol | | | | | 234 | |
| N-ethyl-2-aminoethanol | | | | | | 267 |
| 98% H$_2$SO$_4$ | | | | | | 330 |
| 20% oleum | | 98.5 | | | | |
| ClSO$_3$H | 122.3 | | 192.2 | 245 | 268 | |
| HCl | 38.3 | | 60.2 | 80.3 | | 120.5 |
| HBr | | 89 | | | | |
| H$_2$O | 210 | | 280 | 400 | 466 | 615 |
| VARIATION OF PROCESS, no. of steps | 1 | 2 | 1 | 1 | 1 | 2 |
| REACTION CONDITIONS | | | | | | |
| Sulfation Step: | | | | | | |
| Temperature, ° C. | | 150 | | | | 175 |
| Time, hours | | 3 | | | | 4 |
| Pressure, mm Hg | | 1 | | | | 0.2 |
| Hydrohalogenation Step: | | | | | | |
| Temperature ° C. | 145 | 140 | 135 | 145 | 120–140 | 140 |
| Total Time, hours | 5 | 4 | 5 | 4 | 5 | 5 |
| YIELD OF 2-AMINOALKYL HALIDE BISULFATE SALT(%) | 97 | 95 | 89 | 87 | 92 | 93 |

The cationic starch product thus prepared was dispersed in water at 100° C. and the resulting stable aqueous solution used as a retention aid for TiO$_2$ in the preparation of paper sheets.

In general, the preparation of paper sheets involves forming a slurry of ground cellulose pulp and TiO$_2$ (and alum, if necessary) in water. The slurry is then filtered over a wire screen, and a mat of paper is obtained therefrom. Some of the TiO$_2$ is lost in the filtration process, making it desirable to add a retention aid to the slurry prior to filtration.

In Table IV the results are given for preparing paper sheets both with and without the use of the cationic starch product of this example (N,N-diethyl-2-aminoethyl ether starch) as a retention aid. The amount of TiO$_2$ added to the slurry was 10%, based on the weight of the pulp, and the cellulose used was stock bleached softwood pulp. Alum was added in the amounts specified.

TABLE IV

| Retention Aid | Amount of Retention Aid Employed (% by weight) | Amount of TiO₂ Retained (% by weight) | | |
|---|---|---|---|---|
| | | 0% Alum | 4% Alum | 11% Alum |
| None | 0 | 26 | 40 | 33 |
| Cationic Starch Product | 0.25 | 60 | 53 | 48 |

As the data clearly indicate, the trial employing the cationic starch product shows improved retention of TiO₂ over the control.

Summarizing, this invention is seen to provide a new and improved process for preparing 2-aminoalkyl halide bisulfate salts in high yields whereby 2-aminoalkyl monosulfate esters are reacted with dry hydrogen halide.

Now that the preferred embodiments of the present invention have been described in detail, various modifications and improvements thereon will become readily apparent to those skilled in the art. Accordingly the spirit and scope of the present invention are to be limited only by the appended claims, and not by the foregoing specification.

I claim:

1. A process for preparing 2-aminoalkyl halide bisulfate salts of the general formula:

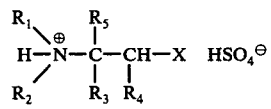

wherein $R_1$ is selected from the group consisting of alkyl ($C_1$ to $C_{18}$), cycloalkyl and hydrogen; $R_2$ is selected from the group consisting of alkyl ($C_1$ to $C_{18}$) and cycloalkyl; $R_3$, $R_4$ and $R_5$ are selected independently from the group consisting of alkyl ($C_1$ to $C_3$) and hydrogen; and X is selected from the group consisting of Cl and Br, said process comprising reacting dry hydrogen halide, selected from the group consisting of hydrogen chloride and hydrogen bromide, in an amount ranging from about stoichiometric to 15 mole percent excess, under essentially anhydrous conditions, with the corresponding 2-aminoalkyl monosulfate ester of the general formula:

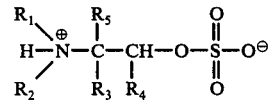

wherein $R_1$, $R_2$, $R_3$, $R_4$ and $R_5$ are all as defined above, the reaction being maintained at about 100° – 200° C.

2. The process of claim 1 wherein said hydrogen halide is hydrogen chloride.

3. The process of claim 1 wherein said hydrogen halide is hydrogen bromide.

4. The process of claim 1 wherein said 2-aminoalkyl halide bisulfate salt is N,N-diethyl-2-aminoethyl chloride bisulfate salt.

5. The process of claim 1 wherein said 2-aminoalkyl halide bisulfate salt is N,N-dimethyl-2-aminopropyl chloride bisulfate salt or N,N-dimethyl-2-aminoethyl bromide bisulfate salt.

6. The process of claim 1 wherein said 2-aminoalkyl halide bisulfate salt is N-methyl-2-aminoethyl chloride bisulfate salt or N,N-dimethyl-2-aminoethyl chloride bisulfate salt.

7. The process of claim 1 wherein the reaction is carried out neat.

8. The process of claim 1 wherein said reaction is carried out at a temperature of 120° – 150° C.

9. The process of claim 1 wherein said 2-aminoalkyl monosulfate ester and said hydrogen halide are prepared in situ by reacting the corresponding halosulfonic acid with a 2-aminoalcohol, or its hydrohalide salt, of the general formula:

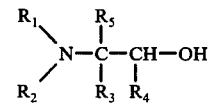

wherein $R_1$, $R_2$, $R_3$, $R_4$ and $R_5$ are all as defined above and said hydrohalide salt thereof is a hydrochloride or hydrobromide salt, with the reaction being carried out for a total of about 3 – 9 hours, at 100° – 200° C. under essentially anhydrous conditions, and the amount of said halosulfonic acid employed ranging from about stoichiometric to 15 mole percent excess.

10. The process of claim 9 wherein said hydrohalide salt is reacted with said halosulfonic acid and the process is repeated, with the hydrogen halide generated in the initial reaction being reacted with additional 2-aminoalcohol to produce additional hydrohalide salt.

11. The process of claim 1 wherein said 2-aminoalkyl monosulfate ester is prepared in a separate step with said hydrogen halide being added directly thereto, with the reaction being carried out for a total of about 3 – 7 hours.

12. The process of claim 9 wherein said reaction is carried out at a temperature of 120° – 150° C.

13. The process of claim 1 wherein the yield of said 2-aminoalkyl halide bisulfate salt is above 85%.

14. The process of claim 1 wherein subsequent to formation of the product, water is added to the reaction mixture and the product recovered as a dissolved salt.

* * * * *